United States Patent
Yamaguchi et al.

(10) Patent No.: US 7,488,839 B2
(45) Date of Patent: Feb. 10, 2009

(54) FLUORINATED ORGANOSILICON COMPOUNDS AND FLUOROCHEMICAL SURFACTANTS

(75) Inventors: Hiromasa Yamaguchi, Annaka (JP); Hirofumi Kishita, Annaka (JP); Koichi Yamaguchi, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 447 days.

(21) Appl. No.: 11/435,766

(22) Filed: May 18, 2006

(65) Prior Publication Data

US 2006/0264596 A1 Nov. 23, 2006

(30) Foreign Application Priority Data

May 20, 2005 (JP) ............................. 2005-147684

(51) Int. Cl.
*C07F 7/08* (2006.01)
(52) U.S. Cl. ............................. 556/446; 528/35; 528/42; 556/431; 556/435; 556/445
(58) Field of Classification Search ........................ None
See application file for complete search history.

(56) References Cited

U.S. PATENT DOCUMENTS 4,689,181 A * 8/1987 Blatch .......................... 554/77

FOREIGN PATENT DOCUMENTS

| JP | 9-241381 A | 9/1997 |
| JP | 10 077421 A | 3/1998 |
| JP | 11 005944 A | 1/1999 |

* cited by examiner

*Primary Examiner*—Marc S Zimmer
(74) *Attorney, Agent, or Firm*—Birch, Stewart, Kolasch & Birch, LLP

(57) ABSTRACT

Fluorinated organosilicon compounds having formula (1) wherein Rf is a perfluoroalkyl group containing at least one ether bond, Q is a polyether group in the form of a homopolymer chain of ethylene glycol or propylene glycol or a copolymer chain of both, R is hydrogen or alkyl, X is a divalent linking group exclusive of oxygen atom, Y is a divalent linking group, p is an integer of at least 3, and n is a number of $0 < n < 3$ have an excellent surface tension reducing ability and can be produced with ease of molecular weight control while minimizing formation of solvent-insoluble components. These compounds are safe to the human body and useful as a surfactant.

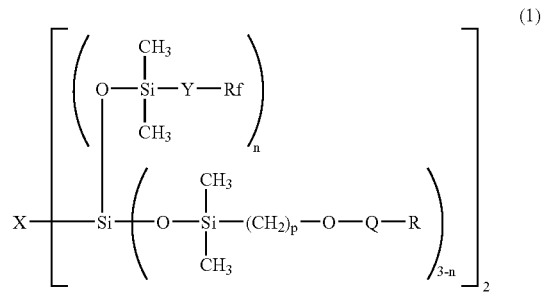

4 Claims, 1 Drawing Sheet

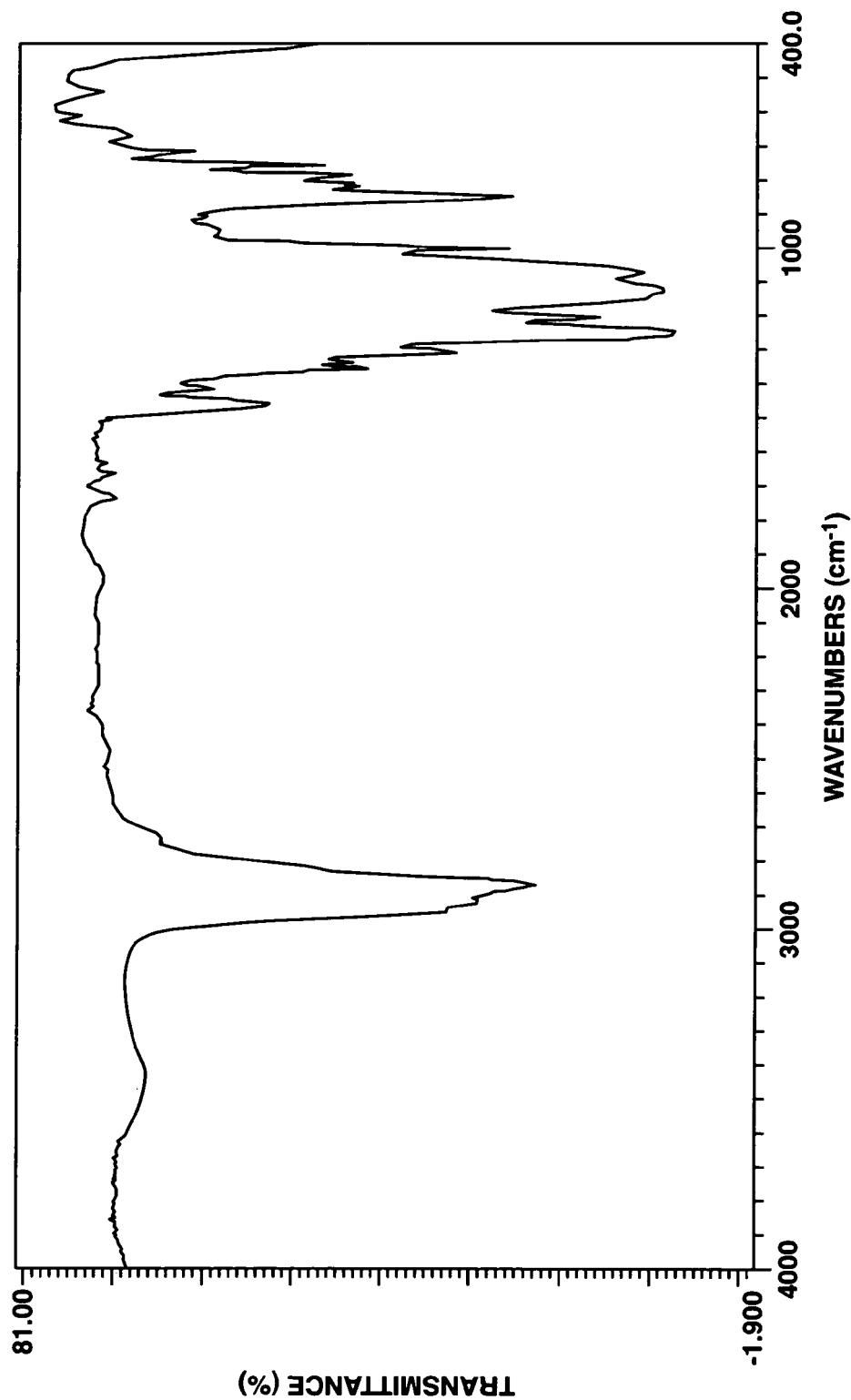

FLUORINATED ORGANOSILICON COMPOUNDS AND FLUOROCHEMICAL SURFACTANTS

CROSS-REFERENCE TO RELATED APPLICATION

This non-provisional application claims priority under 35 U.S.C. §119(a) on Patent Application No. 2005-147684 filed in Japan on May 20, 2005, the entire contents of which are hereby incorporated by reference.

TECHNICAL FIELD

This invention relates to novel fluorinated organosilicon compounds and fluorochemical surfactants.

BACKGROUND ART

Fluorochemical surfactants known in the art are generally prepared by starting with perfluoroalkylsulfonyl fluorides (e.g., $C_8F_{17}SO_2F$), perfluoroalkylcarbonyl fluorides (e.g., $C_7F_{15}COF$) and the like resulting from electrolytic fluorination, and incorporating polyether groups therein via amide or ester groups. These fluorochemical surfactants are often used as a leveling agent in photoresist materials since they have an ability to reduce surface tension markedly when used in small amounts.

However, the reaction involved in the above process has a problem that the percent yield of perfluoroalkyl derivatives of six or more carbon atoms which are useful as surfactants is very low. Another problem is that perfluoroalkyl-containing carboxylic esters (e.g., $C_7F_{15}COOR$) are prone to hydrolysis and unstable.

Also well known in the art are polyether surfactants which are obtained by reacting perfluoroalkyl carbinols with ethylene oxide. This reaction is not regarded satisfactory because it is difficult to control the degree of polymerization of ethylene oxide.

The present inventor previously proposed in JP-A 9-241381 fluorinated organosilicon compounds capable of reducing surface tension markedly. These compounds have the problems that their preparation process is not fully satisfactory in safety because the process involves dehydrogenation condensation reaction, and a fluorinated group/hydrophilic group ratio is not easily changeable.

Also, the above preparation process which involves hydrolytic condensation reaction is difficult to control the molecular weight, especially in a low molecular weight range and leads to a wider distribution of fluorinated group/hydrophilic group ratio, failing to avoid formation of components which are less soluble in solvents. Such insoluble components are unwanted because they become the cause of product deficiencies known as foreign particles in precision electronic material applications including photoresist and the like.

DISCLOSURE OF THE INVENTION

An object of the present invention is to provide fluorinated organosilicon compounds and fluorochemical surfactants, which can reduce surface tension significantly and have overcome the above problems.

The inventor has found that a novel fluorinated organosilicon compound having the general formula (1):

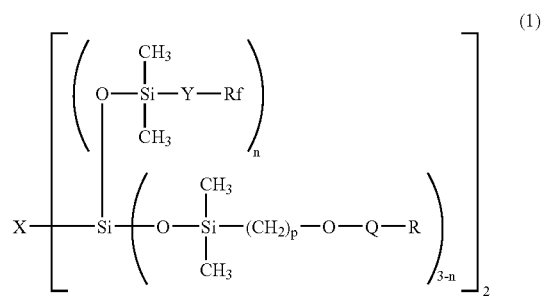

(wherein Rf is a perfluoroalkyl group of 5 to 30 carbon atoms containing at least one ether bond in the molecular chain, Q is a polyether group in the form of a homopolymer chain of ethylene glycol or propylene glycol or a copolymer chain of both, R is hydrogen or an alkyl group of 1 to 4 carbon atoms, X is a divalent linking group exclusive of oxygen atom, Y is a divalent linking group, p is an integer of at least 3, and n is a number of 0<n<3) can be prepared by hydrosilylation reaction of an organosilicon compound having the formula (3):

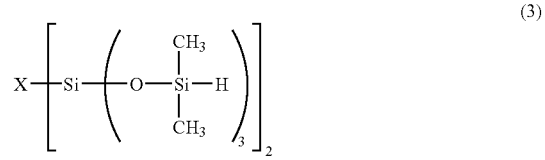

(wherein X is as defined above) with a perfluoropolyether-containing organic compound having a reactive unsaturated hydrocarbon linkage at one end and a polyether compound having the general formula (4):

$$CH_2=CH-(CH_2)_{p-2}-O-Q-R \qquad (4)$$

(wherein p, Q and R are as defined above) in the presence of a platinum base catalyst. Because of the possible synthesis of the fluorinated organosilicon compound having formula (1) by hydrosilylation reaction, it is easy to control the molecular weight in a low molecular weight range, and the desired compound can be produced in a commercially advantageous fashion while minimizing formation of solvent-insoluble components. The fluorinated organosilicon compound of formula (1), typically one with a fluorine content of 7 to 35% by weight, a polyether content of 15 to 55% by weight, and especially a HLB of 4.0 to 10.0, has an excellent surface tension reducing ability and is useful as a surface active agent. The invention is predicated on these findings.

Accordingly, one embodiment of the present invention is a fluorinated organosilicon compound having the general formula (1) defined above. Another embodiment is a fluorochemical surfactant comprising the fluorinated organosilicon compound of formula (1) having a fluorine content of 7 to 35% by weight and a polyether content of 15 to 55% by weight, and preferably a hydrophilic-lipophilic balance (HLB) of 4.0 to 10.0.

BENEFITS OF THE INVENTION

The fluorinated organosilicon compounds of the invention have an excellent surface tension reducing ability and can be produced in a commercially advantageous fashion with ease of molecular weight control while minimizing formation of solvent-insoluble components. These compounds are useful as a surfactant, particularly in precision electronic material applications including photoresist and the like.

BRIEF DESCRIPTION OF THE DRAWINGS

FIG. 1 is an IR spectroscopy chart of the organosilicon compound obtained in Synthesis Example 1.

DESCRIPTION OF THE PREFERRED EMBODIMENTS

One embodiment of the present invention is a fluorinated organosilicon compound having the general formula (1).

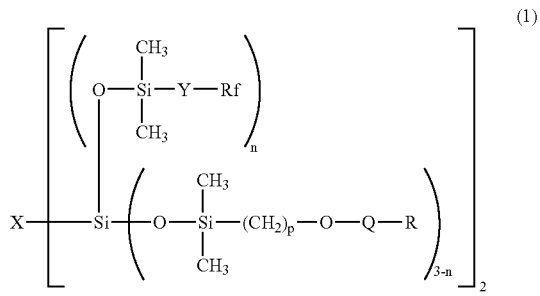

Herein Rf is a perfluoroalkyl group of 5 to 30 carbon atoms containing at least one ether bond in the molecular chain, Q is a polyether group in the form of a homopolymer chain of ethylene glycol or propylene glycol or a copolymer chain of ethylene glycol and propylene glycol, R is hydrogen or an alkyl group of 1 to 4 carbon atoms, X is a divalent linking group exclusive of oxygen atom, Y is a divalent linking group, p is an integer of at least 3, and n is a number of $0<n<3$.

More particularly, Rf is a perfluoroalkyl group of 5 to 30 carbon atoms, preferably 8 to 20 carbon atoms, containing at least one ether bond in the molecular chain. If the number of carbon atoms is more than the range, the compound has a higher molecular weight as a whole and becomes less soluble in solvents, which is undesirable for surfactant use. If the number of carbon atoms is less than the range, the feature of fluorinated group does not develop to a full extent, failing to provide a high interfacial activity.

Illustrative examples of Rf are given below.

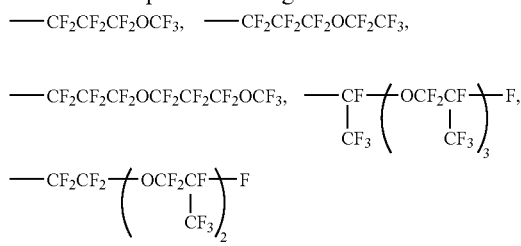

The preferred groups of Rf have the following formula (2):

wherein s is an integer of 1 to 9, especially 2 to 5.

The organosilicon compound of formula (1) wherein Rf is a perfluoroalkyl group containing at least one ether bond according to the invention has a greater surface tension reducing ability than organosilicon compounds modified with a perfluoroalkyl group, provided that the degree of fluorine modification is the same. This leads to the advantage that smaller addition amounts achieve the same effect.

In formula (1), Q is a polyether group which may be formed of a homopolymer chain of ethylene glycol, a homopolymer chain of propylene glycol or a copolymer (block or random copolymer) chain of ethylene glycol and propylene glycol. A proper choice of polymer chain may be made depending on a particular application of the fluorinated organosilicon compound.

The polyether group has a degree of polymerization which may be determined in view of a balance with the hydrophobic fluorinated organic group Rf. When a homopolymer chain of ethylene glycol is used, its degree of polymerization is preferably from 3 to 20, more preferably from 3 to 12. When a homopolymer chain of propylene glycol which is less hydrophilic than ethylene glycol is used, a polymer chain with a relatively high degree of polymerization is preferred, with a degree of polymerization of 100 to 200 being more preferred. In the case of a copolymer chain of ethylene glycol and propylene glycol, the content of propylene glycol is usually in a range of 0 to 50 mol %, preferably 2 to 10 mol %, based on the entire polyether group.

Illustrative examples of Q are given below.

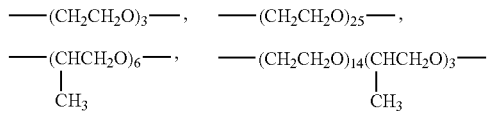

R is hydrogen or an alkyl group of 1 to 4 carbon atoms. Exemplary of the alkyl group are methyl, ethyl, n-propyl, isopropyl, n-butyl, and isobutyl. Preferably R is hydrogen, methyl or n-butyl.

X is a divalent linking group exclusive of oxygen atom. Typical divalent linking groups are alkylene and fluorinated alkylene groups of 2 to 10 carbon atoms. Of these, ethylene, —CH$_2$CH$_2$C$_6$F$_{12}$CH$_2$CH$_2$— and the like are most preferred because the corresponding compounds are easy to prepare.

Y is a divalent linking group. Typical divalent linking groups are alkylene groups of 2 to 10 carbon atoms which may be separated by an ether bond (—O—) or which may be separated by a carbonyl group, imino group or —CONH— group. Illustrative examples of the divalent linking groups are given below.

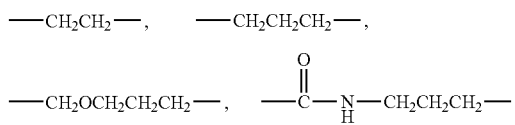

The subscript p is an integer of greater than or equal to 3. The moiety: —(CH$_2$)$_p$— is preferably an alkylene group of 3 or more carbon atoms, more preferably 3 to 6 carbon atoms, most preferably propylene because the corresponding compounds are easy to prepare.

The subscript n is a number from more than 0 to less than 3 (0<n<3). The properties of the inventive organosilicon compound can be controlled by varying the value of n.

The fluorinated organosilicon compound of the invention has the advantage that the properties of the compound serving as a surfactant can be controlled by varying the value of n as mentioned just above. When the fluorinated organosilicon compound of formula (1) is used as a surfactant, it should preferably have a fluorine content of 7 to 35% by weight, more preferably 9 to 30% by weight and a polyether content of 15 to 55% by weight, more preferably 30 to 45% by weight. Even more preferably, the fluorinated organosilicon compound should have a hydrophilic-lipophilic balance (HLB) in the range of 4.0 to 10.0, and especially 5.5 to 9.5. When the fluorine content and the polyether content are within the above ranges, and even more preferably the HLB is within the above range, the compound has a greater surface tension reducing ability and a better balance of surface tension reducing ability and solvent solubility and thus becomes more effective as a surfactant.

If the fluorine content and/or the HLB is below the indicated value, the compound may fail to fully exert water and oil repellent properties inherent to fluorine, lacking somewhat the surface activating function. If the fluorine content and/or the HLB is above the indicated value, the compound may become less soluble in solvents, failing to play the role of surfactant.

It is noted that the HLB is calculated according to the equation:

$$HLB = [\{(Mw \text{ of ethylene oxide chain})/(Mw \text{ of compound})\} \times 100]/5$$

wherein Mw is molecular weight.

The fluorinated organosilicon compound of formula (1) can be readily prepared, for example, by effecting hydrosilylation reaction of an organosilicon compound having the formula (3):

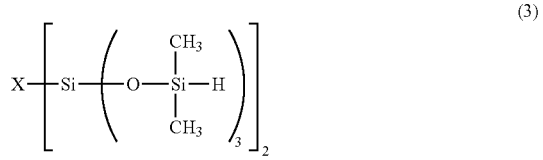

(3)

wherein X is as defined above with a fluorinated organic compound terminated with a reactive unsaturated hydrocarbon linkage and a polyether compound having the general formula (4):

CH$_2$=CH—(CH$_2$)$_{p-2}$—O-Q-R    (4)

wherein p, Q and R are as defined above in the presence of a platinum base catalyst.

The fluorinated organic compound terminated with a reactive unsaturated hydrocarbon linkage may be a compound of the formula: Y'—Rf corresponding to —Y—Rf in formula (1) wherein Y' is a group that has a CH$_2$=CH group at one end and becomes Y when hydrogen is added thereto.

In the hydrosilylation reaction, the mixing proportion of the organosilicon compound of formula (3), the fluorinated organic compound terminated with a reactive unsaturated hydrocarbon linkage, and the polyether compound of formula (4) may be suitably adjusted. When the fluorinated organosilicon compound is used as a surfactant, the mixing proportion is preferably adjusted so as to reach a fluorine content and a polyether content and additionally a HLB in the desired ranges.

With respect to the platinum base catalyst, any of platinum and platinum compounds which are commonly employed in hydrosilylation reaction may be used in a catalytic amount.

Hydrosilylation reaction may be effected under standard conditions, preferably at room temperature to 140° C. for about 0.5 to 6 hours.

The fluorinated organosilicon compound of the invention in which a plurality of fluorine-modified groups and hydrophilic groups are attached to a single silicon atom is effective in reducing surface tension significantly even when used in smaller amounts, as compared with common fluorochemical surfactants of the structure in which a fluorine-modified group and a hydrophilic group are attached one by one. Therefore, the fluorinated organosilicon compound of the invention is more useful as a fluorochemical surfactant. When the fluorinated organosilicon compound of the invention is used as a fluorochemical surfactant, the fluorinated organosilicon compound of formula (1) having a fluorine content and a polyether content and preferably a HLB in the desired ranges may be used singly or in combination of two or more.

On use as a surfactant, the fluorinated organosilicon compound of formula (1) may be added to various solvents, typically organic solvents. Suitable organic solvents include ethyl lactate, propylene glycol monomethyl ether acetate and methyl 3-methoxypropionate. The fluorinated organosilicon compound of formula (1) is preferably present in a concentration of 10 ppm to 1.0% by weight.

The fluorochemical surfactant comprising the fluorinated organosilicon compound of formula (1) has an increased ability to impart or improve many properties including wetting, penetrating, extending, foam stabilizing, flowing, leveling, antifoaming, emulsifying, dispersing, water repellent and oil repellent properties, when added to various liquids, typically organic solvents. The fluorochemical surfactant will thus find many applications as described below. The possible applications include emulsifiers for polymerization, latex stabilizers, foam stabilizers for polyurethane foam or the like, ancillary agents for powder fluorocarbon polymer agglomerates, foaming additives for controlling spreading or coating variations, parting agents for improving mold release during molding, additives for imparting water repellent and oil repellent properties to grease, internal antistatic agents for polyolefins, anti-sweating agents, and anti-blocking agents in the plastic and rubber industry field; additives for improving the flow upon recovery of heavy oil from oil reservoirs, additives for improving the wear resistance of lubricating oil, anti-freezing additives in gasoline carburetors, and agents for inhibiting the evaporation of gasoline and jet fuel by film formation in the petroleum industry field; flow-improving additives for improving the melt spinning step, carbonizing aids for wool, additives for reducing the surface tension of an aqueous solution of synthetic size polyvinyl alcohol (PVA) in the spinning/sizing step, mercerizing assistants, and dyeing finish assistants in the textile industry field; assistants for improving the coloration and dispersion of pigments, agents for imparting flow-leveling and anti-depressing properties for correcting paint defects, and agents for adjusting the evaporation rate of solvent in paint in the dye and pigment industry field; additives to bright plating baths, additives for metal etching, additives to solder flux, corrosion inhibitors, and anti-misting agents for plating in the metal and machinery industry field; agents for improving the penetration of bactericides, agents for improving the wetting of herbicides and insecticides, emulsion-, dispersion- and spreading-improvers in the pharmaceutical and agricultural chemicals field; additives to cleaners, leveling-improvers for polishes, cosmetics additives, and antistatic agents in the household goods field; additives for imparting flowing and spreading properties to ink, leveling agents in photographic emulsions, antistatic agents in film and film drying assistants in the photographic and printing field; antifoaming agents, leveling agents and coating improvers in liquid crystal compositions, photoresist compositions or the like in the precision electronic material field.

EXAMPLE

Synthesis Examples, Examples and Comparative Examples are given below for further illustrating the invention, but the invention is not limited thereto.

Synthesis Example 1

A flask equipped with a reflux condenser and thermometer was charged with 85.7 g of a SiH-containing polysiloxane having formula (5):

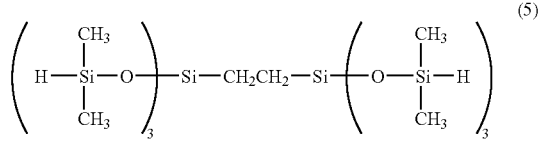

and 105.6 g of toluene, to which 0.18 g of a toluene solution of platinum/vinylsiloxane complex (corresponding to 0.9 mg of Pt) was added. This reaction solution was heated at 80° C., to which 125.4 g of a fluorinated organic compound having a reactive unsaturated hydrocarbon linkage represented by the formula (6):

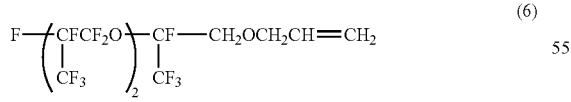

and 147.1 g of a polyether compound represented by the formula (7):

(7)

were added dropwise. At the end of dropwise addition, the reaction solution was held at the temperature for 2 hours. By infrared (IR) spectroscopy, the disappearance of SiH groups was confirmed. The solution was heated under reduced pressure for distilling off the solvent and low-boiling fraction, leaving 320.0 g of a pale brown oily matter.

This oily matter was analyzed by proton-nuclear magnetic resonance ($^1$H-NMR) and IR spectroscopy, with the results shown below.

$^1$H-NMR spectra (TMS standard, ppm):
0-0.1 (36H, Si—CH$_3$), 0.1-0.2 (16H, Si—CH$_2$—),
1.3-1.5 (12H, —CH$_2$—), 3.1 (27H, CH$_3$O—),
3.2-3.5 (72H, —CH$_2$O—)

IR spectra: FIG. 1

With the data, the oily matter was identified to have the structure of the following formula.

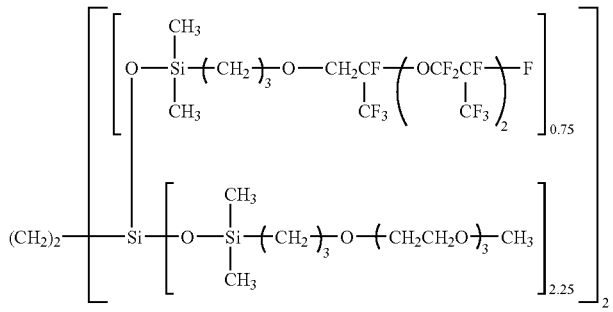

The fluorinated organic compound obtained had a fluorine content, a polyether content and HLB which are reported below in Table 1. It is noted that the HLB is calculated according to the equation: HLB=[{(Mw of ethylene oxide chain)/(Mw of compound)}×100]/5 wherein Mw is molecular weight.

Synthesis Example 2

Reaction was carried out as in Synthesis Example 1 except that 197.8 g of a fluorinated organic compound of the formula (8):

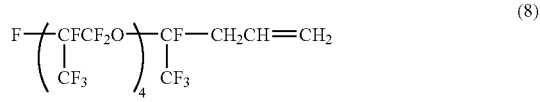

was used instead of the fluorinated organic compound of formula (6) and 253.0 g of a polyether compound having the average compositional formula (9):

(9)

was used instead of the polyether compound of formula (7). There was obtained 513.8 g of a pale brown oily matter. This oily matter was analyzed as in Synthesis Example 1 to find a fluorine content, polyether content and HLB which are reported below in Table 1.

Synthesis Example 3

Reaction was carried out as in Synthesis Example 1 except that 83.6 g of the fluorinated organic compound of formula (6) and 280.7 g of the polyether compound of formula (9) were used. There was obtained 404.1 g of a pale brown oily matter. This oily matter was analyzed as in Synthesis Example 1 to find a fluorine content, polyether content and HLB which are reported below in Table 1.

Synthesis Example 4

Reaction was carried out as in Synthesis Example 1 except that 41.8 g of the fluorinated organic compound of formula (6) and 308.8 g of the polyether compound of formula (9) were used. There was obtained 329.1 g of a pale brown oily matter. This oily matter was analyzed as in Synthesis Example 1 to find a fluorine content, polyether content and HLB which are reported below in Table 1.

Synthesis Example 5 (Comparison)

A flask equipped with a reflux condenser and thermometer was charged with 280.0 g of a SiH-containing polysiloxane having formula (10):

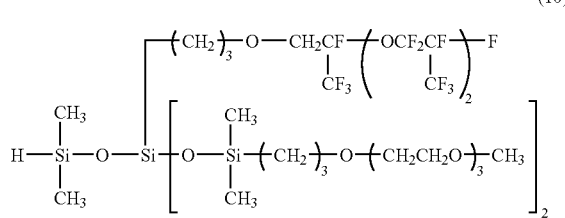

(10)

and 120.0 g of tetrahydrofuran, and heated until an internal temperature of 45° C. was reached. Then 10.0 g of a 1 mole/L sodium hydroxide aqueous solution was added. The reaction took place while generating a noticeable amount of hydrogen gas. The disappearance of the absorption peak assigned to SiH group (at 2130 cm$^{-1}$) was confirmed by IR spectroscopy, after which 11.0 g of 1 mole/L hydrochloric acid was added to quench the reaction. From the reaction solution, the solvent was distilled off in vacuo, and the salt precipitated was filtered out. In this way, 251.3 g of a pale brown oily matter was obtained. This oily matter was analyzed as in Synthesis Example 1 to find a fluorine content, polyether content and HLB which are reported below in Table 1.

Examples 1 to 3

The fluorinated organosilicon compounds obtained in Synthesis Examples 1 to 3 were assessed for several properties on use as surfactant.

Solubility

Using the compounds obtained in Synthesis Examples 1 to 3, 10 wt % solutions in ethyl lactate (EL), propylene glycol monomethyl ether acetate (PGMEA) and methyl 3-methoxypropionate (MMP) were prepared. The solutions were examined for transparency by visual observation and rated according to the following criterion. The results are shown in Table 1.

Solubility Rating

○: fully dissolved and transparent

Δ: slightly white turbid

X: white turbid

Surface Tension

Using the compounds obtained in Synthesis Examples 1 to 3, 0.1 wt % solutions in methyl 3-methoxypropionate (MMP) were prepared. The surface tension of these solutions at 25° C. was determined by Wilhelmy method. The results are shown in Table 1.

Foam Inhibition

To 100.0 g of a 0.5 wt % solution of sodium dodecylbenzenesulfonate was added 0.01 g of each compound obtained in Synthesis Examples 1 to 3. A test liquid was prepared by thorough mixing. The test liquid, 20 ml, was transferred into a test tube of 20 mm inner diameter and 200 mm height, shaken for one minute, and allowed to stand. The foaming state of the liquid after one minute was visually observed and rated according to the following criterion (foam height). The results are shown in Table 1.

Foam inhibition rating

○: little foaming (<20 mm)

Δ: moderate foaming (20-50 mm)

X: vigorous foaming (>50 mm)

Resist Coating Improvement 27 parts by weight of a condensate of 2,3,4-trihydroxybenzophenone with o-naphthoxydiazido-5-sulfonyl chloride and 100 parts by weight of a novolac resin resulting from condensation of cresol and formaldehyde were dissolved in 400 parts by weight of ethyl lactate (EL) to prepare a solution. Each compound obtained in Synthesis Examples 1 to 3 was added to this solution in a concentration of 30 ppm relative to the solids in the solution. The solution was precision filtered through a PTFE membrane filter with a pore size of 0.1 μm, obtaining a photoresist composition. This photoresist composition was spin coated on a silicon wafer having a diameter of 300 mm at 3,600 rpm, which was heated on a hot plate for 60 seconds to remove the solvent, thus forming a resist film of 1.2 μm thick on the wafer. The resist film on the silicon wafer was evaluated for coating characteristics. The results are shown in Table 1.

Resist Coating Rating

○: neither coating variation nor cissing

Δ: slight coating variation and cissing

X: noticeable coating variation and cissing

Reference Example and Comparative Examples 1-2

The compounds obtained in Synthesis Examples 4 and 5, and the compound having the formula (11):

(11)

were tested by the same methods as in Examples. The results are also shown in Table 1.

TABLE 1

| Compound | Example 1 Synthesis Example 1 | Example 2 Synthesis Example 2 | Example 3 Synthesis Example 3 | Reference Example 1 Synthesis Example 4 | Comparative Example 1 Synthesis Example 5 | Comparative Example 2 formula (11) |
|---|---|---|---|---|---|---|
| F content (wt %) | 21.6 | 24.7 | 11.5 | 5.9 | 27.1 | 31.5 |
| Polyether content (wt %) | 26.6 | 37.3 | 49.4 | 56.0 | 22.2 | 42.9 |
| HLB | 5.3 | 7.5 | 9.9 | 11.2 | 4.4 | 8.6 |
| Solubility  EL | ○ | ○ | ○ | Δ | X | ○ |
|  PGMEA | ○ | ○ | ○ | Δ | Δ | ○ |
|  MMP | ○ | ○ | ○ | ○ | Δ | ○ |
| Surface tension | 24.5 | 23.3 | 25.1 | 26.3 | 23.5 | 26.5 |
| Foam inhibition | ○ | ○ | ○ | X | Δ | Δ |
| Resist coating | ○ | ○ | ○ | X | Δ | X |

Japanese Patent Application No. 2005-147684 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A fluorinated organosilicon compound having the general formula (1):

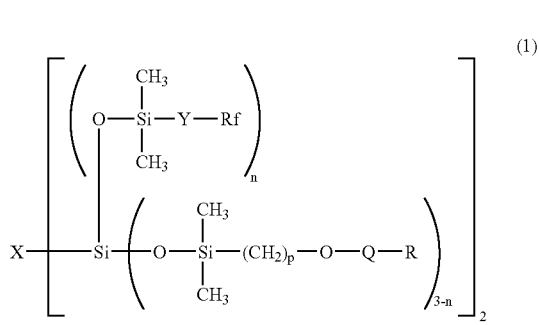

wherein Rf is a perfluoroalkyl group of 5 to 30 carbon atoms containing at least one ether bond in the molecular chain, Q is a polyether group in the form of a homopolymer chain of ethylene glycol or propylene glycol or a copolymer chain of both, R is hydrogen or an alkyl group of 1 to 4 carbon atoms, X is a divalent linking group exclusive of oxygen atom, Y is a divalent linking group, p is an integer of at least 3, and n is a number of 0<n<3.

2. The fluorinated organosilicon compound of claim 1 wherein Rf is a group having the formula (2):

wherein s is an integer of 1 to 9.

3. A fluorochemical surfactant comprising the fluorinated organosilicon compound of formula (1) as set forth in claim 1, having a fluorine content of 7 to 35% by weight and a polyether content of 15 to 55% by weight.

4. The surfactant of claim 3 wherein the fluorinated organosilicon compound has a HLB of 4.0 to 10.0.

* * * * *